United States Patent [19]

Dietz et al.

[11] 4,419,212

[45] Dec. 6, 1983

[54] COMBINATION GAS OXYGEN CONCENTRATION AND COMBUSTION LIGHT SENSOR

[75] Inventors: Hermann Dietz, Gerlingen; Gerhard Holfelder, Weissach-Flacht; Klaus Müller, Tamm; Harald Reber, Gerlingen, all of Fed. Rep. of Germany

[73] Assignee: Robert Bosch GmbH, Stuttgart, Fed. Rep. of Germany

[21] Appl. No.: 343,194

[22] Filed: Jan. 27, 1982

[30] Foreign Application Priority Data

Feb. 7, 1981 [DE] Fed. Rep. of Germany ....... 3104410

[51] Int. Cl.³ .............................................. G01N 27/46
[52] U.S. Cl. .................................... 204/424; 204/426; 204/427; 73/35; 123/494; 250/227
[58] Field of Search ................... 204/1 S, 195 S, 421, 204/424–429; 73/35; 123/425, 435, 494; 250/227

[56] References Cited

U.S. PATENT DOCUMENTS

| | | | |
|---|---|---|---|
| 2,841,979 | 7/1958 | Harbert | 73/35 |
| 2,919,688 | 1/1960 | Bowditch et al. | 356/241 |
| 3,067,610 | 12/1962 | Bockemuehl et al. | 73/35 |
| 3,517,247 | 6/1970 | Szilagyi | 324/395 |
| 4,065,372 | 12/1977 | Hacker et al. | 204/195 S |
| 4,130,097 | 12/1978 | Ford | 123/425 |
| 4,155,828 | 5/1979 | Takao et al. | 204/195 S |
| 4,229,275 | 10/1980 | Habdas et al. | 204/195 S |
| 4,240,893 | 12/1980 | Hamano | 204/195 S |
| 4,247,380 | 1/1981 | McIntyre | 204/195 S |
| 4,369,748 | 1/1983 | Steinke | 73/35 |
| 4,377,086 | 3/1983 | Linder | 250/227 |

FOREIGN PATENT DOCUMENTS

| | | | |
|---|---|---|---|
| 831166 | 2/1952 | Fed. Rep. of Germany | 73/35 |
| 263883 | 8/1927 | United Kingdom . | |

*Primary Examiner*—T. Tung
*Attorney, Agent, or Firm*—Frishauf, Holtz, Goodman & Woodward

[57] ABSTRACT

To permit simultaneous evaluation of the light as a consequence of combustion in the combustion chamber of an internal combustion (IC) engine, and evaluation of the oxygen content of the combustion gas resulting from the combustion, a tubular housing of generally spark-plug shape is closed off at the end facing the combustion chamber by a solid electrolyte body in form of a disk (6), closed tube or thimble (6c) or the like, which is made of transparent zirconium dioxide. The interior of the housing has a light guide (7) extending therein. The solid electrolyte body has electrodes (11, 11'; 11c, 11'c) applied thereto, electrically connected to an electrical evaluation stage (EE) to determine oxygen concentration in the combustion gases, while the light due to combustion is transmitted through the solid electrolyte to the light guide for evaluation in an optical evaluation stage (EO). The ceramic body may be ground to form a lens to focus light resulting upon combustion on the light guide which can have a jacket (15) which is electrically conductive to provide one output terminal from the electrodes applied to the solid electrolyte body, the other electrode being connected through the housing to chassis.

10 Claims, 3 Drawing Figures

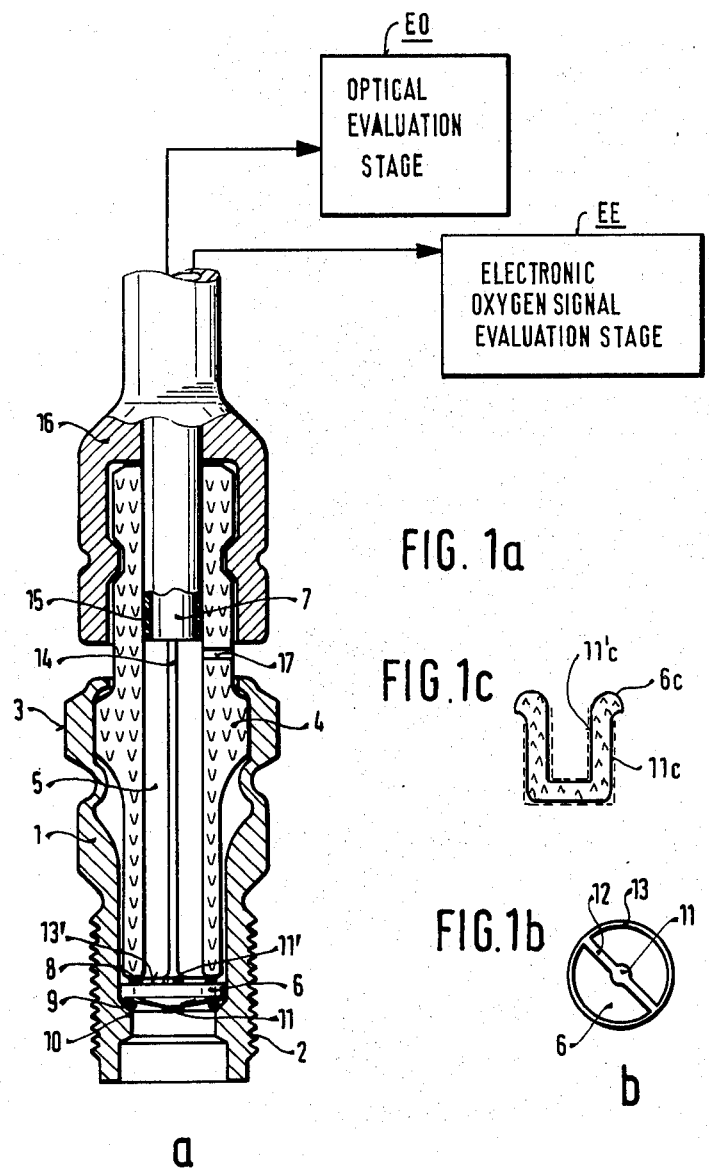

COMBINATION GAS OXYGEN CONCENTRATION AND COMBUSTION LIGHT SENSOR

Reference to related patent and application assigned to the assignee of this invention, and publications, the disclosure of which is hereby incorporated by reference:

U.S. Ser. 06/214,481, now patent 4,393,687, filed Dec. 9, 1980, MULLER, LINDER and MAURER.

"Automotive Handbook", published by Robert Bosch GmbH, Copyright 1976, pp. 275–277.

The present invention relates to a sensing arrangement to sense combustion processes, and more particularly to sense the combustion process within the combustion chamber of an internal combustion engine. The engine may be an Otto-type engine or a Diesel-type engine.

BACKGROUND

It is desirable to determine the course of combustion in internal combustion engines, and various types of scribed in the referenced application Ser. 06/214,481, now patent 4,393,687, is particularly arranged to sense irregular combustion events which may result in knocking. It is known to measure and determine and sense the combustion processes which occur in the combustion chamber of internal combustion engines during operation. It is desirable to sense as many physical parameters as possible. The temporal and spatial spread of the combustion process upon generation of a spark or injection of fuel is desirable, as well as exact sensing of ignition instant, determination and measuring of fuel injection processes, and the spread as well as spatial distribution of irregular combustion processes. The oxygen partial pressure also should be measured.

The referenced application describes a sensor in which, by optical sensing, combustion processes can be determined; it is particularly arranged to sense irregular combustion processes. Various other literature references referred to and summarized in the aforementioned referenced application describe additional sensing arrangements, for example a spectrometric process for investigating and checking the combustion of the fuel-air mixture in a Diesel engine. A quartz window is placed in the wall of the combustion chamber to permit spectrometric observation of the combustion event.

Oxygen partial pressure of combustion gases can be measured in various ways, for example by a potentiometric sensor or a polarographic sensor; potentiometric sensors operate similarly to a fuel cell by providing an output voltage if a reference oxygen partial pressure, for example as derived from oxygen in ambient air, differs from oxygen partial pressure within the sensed environment. Thus, if the environment contains a reducing atmosphere, an output voltage will be obtained which, upon change of the environment to an oxidizing condition, will drop suddenly to approximately null or zero output. Such sensors, also called lambda sensors, are used in connection with sensing the composition of exhaust gases from internal combustion (IC) engines. Other sensors operate in the polarographic mode, in which a limiting current will develop upon application of an external voltage to electrodes applied to the sensor element, the limiting current changing with change in oxygen content of the gas to be sensed. Typically, these sensors include an oxygen ion conductive solid electrolyte which has two boundary surfaces, one of them being exposed to a reference gas, for example ambient air which supplies oxygen, and the other to the gas to be tested for oxygen content. The solid electrolytes used are, customarily, ceramic elements, for example made of stabilized zirconium dioxide, supplied on their boundary surfaces with a gas permeable thin layer of electrode material, typically platinum. The sensor body, that is, the electrolyte with the electrodes applied thereto, may be in form of a closed tube having a sensing end exposed to the gas, in form of a disk, in which one surface is exposed to the gas to be tested, or may have other configuration. Such sensors are well known and described in the literature, see, for example, U.S. Pat. No. 3,841,987, FRIESE et al., and "Automotive Handbook", issued by Robert Bosch GmbH, pp. 275–277, section relating to exhaust gases.

THE INVENTION

It is an object to provide a sensor which permits simultaneously, to observe the combustion process as well as to sense the composition of the resulting combustion gases, and to so arrange the sensor that is can easily be mounted in an internal combustion engine.

Briefly, a solid electrolyte body is positioned in an elongated housing, similar to a spark plug housing, for example, the solid electrolyte body having electrodes applied thereto. In a preferred form, the solid electrolyte body, which is a transparent ceramic of zirconium dioxide, is shaped in the form of a disk, which may be ground in lens shape, to close off the open end of an elongated housing. The electrolyte body has electrodes applied thereto, and connection means lead to a terminal end portion thereof. If in disk shape, the body is retained in the housing by a retention sleeve, for example of ceramic, seating the solid electrolyte ceramic in a sealing ring arrangement. To sense light, a light guide is combined with the sensor structure, the light guide being optically coupled to the combustion chamber and secured in the tubular housing to transmit light signals representative of combustion processes occurring in the combustion chamber, the light guide passing through the tubular housing and being coupled to a light guide cable. The output from the light guide cable can then be evaluated in an opto-electrical transducer or evaluation stage; the output from the electrodes of the solid electrolyte body are evaluated in an electronic oxygen signal evaluation stage, which may be in accordance with any well known and suitable structure.

In a preferred form, the solid electrolyte body is a transparent ceramic and the light guide is coupled to the transparent ceramic to receive light which is being transmitted through the solid electrolyte body while the solid electrolyte body as such acts as an oxygen sensor. The solid electrolyte body, thus, is used to have multiple functions, namely to provide an electrical evaluation of the composition of ambient gases, typically combustion gases, while at the same time acting as a light transmitting element to couple light arising upon combustion to a light guide. The solid electrolyte body, further, protects the light guide fibers from direct contact with the combustion exhaust gases.

The sensor arrangement has the advantage that optical measurement of a combustion event and measurement of the composition of the combustion gases can be done at the same location and at the same time, while permitting construction of a single element which is easily made, for example of the general shape of a spark plug, so that the sensor structure can readily be assembled to an internal combustion engine in well known manner.

DRAWINGS

FIG. 1 is a schematic longitudinal cross-sectional view through a combined exhaust gas composition-optical combustion sensor;

FIG. 1b is a top view of the solid electrolyte element used in the structure of FIG. 1a; and FIG. 1c is a schematic cross-sectional view of another form of a solid electrolyte body.

A metal housing which, generally, may be a in the shape of a spark plug for introduction through the engine block of an IC engine has an external thread 2, so that it can be screwed into an opening in the engine block, and an external hexagonal nut surface 3, for example to permit engagement by a standard spark plug socket wrench. The interior of the elongated tubular metal housing 1 has a ceramic sleeve located therein, which is under compression force. The ceramic sleeve is hollow and surrounds an open space or chamber 5. The chamber 5 is closed off at the combustion chamber end of the housing 1 by a disk 6. The outer or terminal end of the chamber 5 is closed off by a light guide cable 7. The disk 6 is seated in sealing elements 8, 9, for example sealing rings or the like. The housing 1 is formed with an internal shoulder 10, against which the sealing ring or sealing mass 9 is seated. The sealing ring or sealing mass 9 is interposed between the disk 6 and the tubular ceramic compression element 4. The sealing mass 9, preferably, is electrically conductive.

The disk 6 is made of ion conductive ceramic material, for example zirconium dioxide, and has electrodes placed on its two major surfaces—see FIG. 1b. The electrode arrangement is formed by a central electrode 11, 11' which is connected to ring-formed outer contact surfaces 13 by conductive tracks 12 extending in the form of one or more transverse spokes across the disk 6. The contact surface 13 is in electrical contact with the metal housing 1, for example through the electrically conductive seal 9, or by means of a small interposed flexible metal ring, not shown. The contact surface 13', at the inner surface of the disk 5, is connected to a conductor 14 which extends up to the light guide cable 7 and is there connected to a metal strand included in the light guide cable or to a conductive jacket or woven cover 15, which is externally insulated, for example similar to a coaxial cable. The outer end of the sensor is protected by a flexible closure cap 16, for example of rubber or plastic material, which also protects and secures the light guide cable 7 and the associated electrical conductor portions connected to the conductor 14 in position. A transverse bore 17 is formed in the ceramic compression sleeve 4 to provide access of ambient air to the upper surface of the disk 6, and thus provide a reference oxygen environment.

Operation: Light which occurs in the combustion chamber of an IC engine is passed through the disk 6 into the chamber 5 and will meet the exposed end surface of the light guide cable 7 so that optical observation of the combustion event in the combustion chamber is entirely feasible. The space 5 need not be empty; it can be filled with a temperature-stable light guide element, for example quartz glass, wholly or in part; such a fill is not shown for clarity of illustration. The filler does not interfere with access of ambient air, for reference, to the electrode 11'.

Disk 6 is made of oxygen ion conductive solid electrolyte material, for example zirconium oxide ceramic, and thus acts as a lambda sensor. The surface of disk 6 which faces the combustion chamber, and to which electrode 11 is applied, is exposed to combustion gases; the surface of disk 6 facing the chamber 5 is exposed to the reference gas which can enter the chamber 5 through the opening 17.

The disk 5 is made of zirconium dioxide ceramic which is transparent or at least translucent. In accordance with a feature of the invention, the disk 5 is ground to form a lens—see FIG. 1a— to focus light falling on the combustion chamber side of disk 6 on the end surface of light guide cable 7 or on such other light guide element as may be contained in the chamber 5, for example a quartz glass rod, which may have a central opening through which conductor 14 extends, which also can assist in holding the rod in place. The ceramic body need not be in disk form, however, but may also be in form of a closed tube, for example of a shape similar to a small thimble which extends from the chamber 5 towards the combustion chamber where combustion gas composition, as well as light arising upon combustion, is to be sensed.

The electrical connection from conductor 14 extends to an electronic oxygen signal evaluation stage EE, for example of suitable and well known construction, which evaluates the output signals derived from the sensor. The light guide cable is coupled to an optical evaluation stage EO, which evaluates the optical signals and may, for example, include an opto-electronic coupler, such as a light sensitive diode or the like. The electronic oxygen signal evaluation stage EE may also be used to supply an external voltage to the electrodes 11, 11' is the sensor is to operate in a polarographic sensing mode.

As best seen in FIG. 1b, the electrodes are preferably located centrally on the disk 6; they are made, for example, of a thin film of porous and transparent or translucent platinum. If the solid electrolyte body is made in the shape of a thimble or closed tube (see FIG. 1c), the outer electrode 11c and/or the inner electrode 11'c may cover the side portions of the thimble-shaped body 6c to provide greater electrode surface without, in this structure, interfering with light transmission through the bottom portion of the thimble-like structure 6c. The bottom of the solid electrolyte body structure 6c may, of course, be shaped to form a lens similar to the lens of the disk 6.

Various changes and modifications may be made, and features described in connection with any one of the embodiments may be used with the others within the scope of the inventive concept.

Since the electrodes 11, 11c are preferably made of platinum, or a platinum group metal, they additionally contribute to keeping the light transmissive body 6, 6c free from accumulated contamination by soot and the like since, upon the presence of oxygen, any accumulated carbon or soot will burn off from the surface of the solid electrolyte 6, 6c due to the catalyzing effect of the platinum or platinum metal of the electrode (see also U.S. patent application, Ser. No. 62.361-SARHOLZ).

We claim:

1. Unitary oxygen concentration and combustion light sensor to determine (a) light emission phenomena upon combustion of a fuel-air mixture in a combustion chamber, especially the combustion chamber of an internal combustion (IC) engine; and (b) the concentration of oxygen in resulting combustion gases, having an elongated tubular housing (1) formed with attachment means (2, 3) to expose one end of the housing to the combustion chamber comprising, in accordance with the invention, the combination of a solid electrolyte body of a light transmission ceramic material (6) positioned in the housing;

electrodes (11, 11', 11c, 11'c, 12) applied to the solid electrolyte body;

and connection means (9, 14, 15) connected to the electrodes for forming externally accessible terminals to apply signals derived from said electrode to an electronic oxygen signal evaluation stage (EE) to evaluate the oxygen content of the gases resulting from combustion of the fuel-air mixture in the combustion chamber;

with a light guide (7) positioned in optically coupled relation to the combustion chamber and secured in the tubular housing, to transmit light signals representative of combustion processes in the combustion chamber to an optical combustion process evaluation stage (EO) to optically evaluate the combustion process upon occurrence of combustion of said fuel-air mixture for conjoint and simultaneous sensing of changes in chemical composition of the atmosphere in the combustion chamber upon occurrence of combustion and the optical phenomena of said combustion.

2. Sensor according to claim 1, wherein the solid electrolyte body (6, 6c) is optically coupled to said light guide (7) to guide light transmitted through said body outside of the housing.

3. Sensor according to claim 2, wherein the solid electrolyte ceramic comprises stabilized zirconium dioxide.

4. Sensor according to claim 2, wherein said solid electrolyte ceramic body comprises a transparent or translucent disk closing off the end of the tubular housing adjacent the combustion chamber.

5. Sensor according to claim 4, wherein said transparent or translucent disk comprises an optical lens focussing light incipient on said body on the light guide.

6. Sensor according to claim 2, wherein the solid electrolyte ceramic comprises a thimble-like or closed tubular structure (6c).

7. Sensor according to claim 1, wherein said housing (1) defines a chamber (5) within its interior, the solid electrolyte body (6, 6c) closing off said chamber (5) with respect to the combustion chamber;

and means (17) applying reference oxygen to said chamber (5) and hence to the side of the ceramic body remote from the combustion chamber.

8. Sensor according to claim 1, wherein said tubular housing (1) defines a chamber (5) therein, said solid electrolyte body (6, 6c) closing off the chamber (5) with respect to the combustion chamber;

and electrodes (11, 11', 11'c) located, respectively, at the sides facing the combustion chamber and said chamber (5) inside the tubular housing, the connection means (9, 14, 15) being in electrical connection with respective ones of the electrodes.

9. Sensor according to claim 8, wherein the electrodes comprise spot or dot-like regions of porous metal;

and conductive tracks (12, 12') extend from said spot or dot-like electrodes to marginal regions of said solid electrolyte body for connection to said connection means.

10. Sensor according to claim 8, wherein the electrodes comprise porous translucent or transparent thin-film metal electrodes applied to at least portions of said ceramic body, and in electrically conductive communication with said connection means.

* * * * *